US00PP12534P2

(12) United States Plant Patent

Olesen et al.

(10) Patent No.: US PP12,534 P2
(45) Date of Patent: Apr. 9, 2002

(54) FLORIBUNDA ROSE PLANT NAMED 'POULREB'

(76) Inventors: L. Pernille Olesen; Mogens N. Olesen, both of Hillerodvejen 49, Fredensborg DK-3480 (DK)

( * ) Notice: Subject to any disclaimer, the term of this patent is extended or adjusted under 35 U.S.C. 154(b) by 0 days.

(21) Appl. No.: 09/287,295

(22) Filed: Mar. 31, 1999

(51) Int. Cl.[7] ..... A01H 5/00
(52) U.S. Cl. ..... Plt./145
(58) Field of Search ..... Plt./145, 141, 144

(56) References Cited

U.S. PATENT DOCUMENTS

PP9,657 P * 10/1996 Zary ..... Plt./145

OTHER PUBLICATIONS

UPOV–ROM GTITM Computer Database 2000/06, Dec. 8, 2000, GTI Jouve Retrieval Software, Citation for 'POULreb'.*
Controller of Plant Variety Rights "Grant of Plant Breeders' Rights" Mar. 20, 1995 1 page UK.
Research Center for Cultivar Testing "Decision" Feb. 22, 1998, Poland.
Plant Novelty Agency "Notice of Protection of Plant Novelty" Feb. 3, 1999, 1 page Denmark.
Plant Novelty Agency "Plant Novelty" 1993 p. 464 *Gartner Tidende* 1 page Denmark.
Plant Novelty Agency "Registration of Plant Novelty in Acordance With Plant Novelty Law" Dec. 1, 1992 3 pages. Denmark.
Community Plant Variety Office "Certificate On The Grant of Community Plant Variety Rights" Aug. 2, 1996, 7 pages.
Community Plant Variety Office "Receipt" Aug. 3, 1995 6 pages EU.

* cited by examiner

*Primary Examiner*—Bruce R. Campell
*Assistant Examiner*—June Hwu

(57) ABSTRACT

A new garden rose plant which has abundant, yellow flowers and attractive foliage. This new and distinct variety has shown to be uniform and stable in the resulting generations from asexual propagation.

1 Drawing Sheet

SUMMARY OF THE INVENTION

The present invention constitutes a new and distinct variety of garden rose plant which originated from a controlled crossing during the summer of 1988 between an unnamed seedling (non-patented) and an unnamed seedling (non-patented). The two parents were crossed and the resulting seeds were planted in a controlled environment. The new variety is named 'POULreb'.

The new rose may be distinguished from its seed parent, an unnamed seedling, by the following:

The seed parent is a grandiflora with yellow and red bi-colored flowers, while 'POULreb' is a yellow floribunda.

The new variety may be distinguished from its pollen parent, an unnamed seedling created by the same inventors, by the following:

The pollen parent is a floribunda with amber yellow flowers, while 'POULreb' is a yellow floribunda.

The objective of the hybridization of this rose variety for garden use was to create a new and distinct variety with unique qualities, such as:

1. Uniform and abundant flowers;
2. Vigorous, compact growth;
3. Cold hardiness and disease resistance.

This combination of qualities is not present in previously available commercial cultivars of this type and distinguish 'POULreb' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULreb' was selected by the inventors in the spring of 1989 as a single plant from the progeny of the aforementioned hybridization.

Asexual reproduction of 'POULreb' by traditional budding was first done by L. Pernille and Mogens N. Olesen in their nursery in Fredensborg, Denmark in August, 1989. This initial and other subsequent propagations conducted in controlled environments have demonstrated that the characteristics of 'POULreb' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULreb'. Specifically illustrated in SHEET 1:

1. Stem showing branching and the attachment of leaves, buds, and peduncles;
2. Flower bud, partially opened bud, and open bloom;
3. Flower petals, detached;
4. Sepals, receptacle, and pedicel;
5. Flowering stem as well as a bare stem exhibiting thorns;
6. Leaves.

DETAILED DESCRIPTION OF THE VARIETY

The following is a description of 'POULreb', as observed in its outdoor growth in a field nursery in Jackson County, Oreg., on plants aged eighteen months. Observations were conducted during August, 1998. Color references are made using The Royal Horticultural Society (London, England) Colouor Chart, 1995, except where common tems of color are used.

For a comparison, several physical characteristics of the rose variety 'POULreb', a floribunda rose variety from the same inventors described and illustrated in U.S. Plant Pat. No. 6,265 and issued on Aug. 30, 1988 are compared to 'POULreb' in Chart 1.

CHART 1

| | 'POULreb' | 'POULander' |
|---|---|---|
| Flower bud color, as sepals first divide. | Yellow Group 4C. | Red Group 46A. |
| Color, upper petal surface, upon opening. | Yellow Group 7B at base, Yellow Group 9D at tip. | Red group 46B to 46C. |
| Petalage under normal conditions. | 60–75 petals. | Approx. 20 petals. |

Parents:
*Seed parent.*—An unnamed seedling.
*Pollen parent.*—An unnamed seedling.
Classification:
*Botanical.*—*Rosa hybrida.*
*Commercial.*—Floribunda.

FLOWER AND FLOWER BUD

Blooming habit: Continuous.
Flower bud:
*Size.*—Upon opening, 30 mm in length from base of receptacle to end of bud.
*Bud form.*—Short and globular.
*Bud color.*—As sepals unfold, Yellow Group 4C. Yellow Group 9C at ¼ opening.
*Sepals.*—Green Group 144B. Weak foliaceous appendages on three of the five sepals. Surfaces of sepals moderately pubescent. Stipitate glands are present in limited numbers on the outer surfaces of the sepal, along the margins of the sepal, and on the foliaceous appendages. Sepals are 20 to 25 mm long and 10 to 13 mm wide. The sepal's apex is cirrose in shape with a flat base.
*Receptacle.*—Surface: Smooth. Shape: Funnel shaped. Size: Small, 8 mm (h)×5 mm (w). Color: Yellow-Green Group 144C.
*Peduncle.*—Surface: With stipitate glands in limited numbers. Length: 120 to 170 mm. Color: Yellow-Green Group 144C, with occasional anthocyanin coloration of Greyed-Red Group 180C. Strength: Strong.
*Borne.*—With 1–6 buds per flowering stem.
Flower bloom:
*Fragrance.*—Strong perfume with classic old rose scent.
*Duration.*—As a cut flower 3 to 5 days. The blooms have a duration on the plant of approximately 5 to 6 days. Petals fall cleanly away from plant.
*Size.*—Average flower diameter is 70–80 mm when open.
*Form.*—Open cup shaped. Shape of flower when viewed from the side: Upon opening, upper part: Flat to flattened convex. Upon opening, lower part: Flat. Open flower, upper part: Flat. Open flower, lower part: Concave.
*Petalage.*—Very double. Average range: 60–75 petals under normal conditions with 20 petaloids.
Color: The occasional petal has a small red strip with the intonation of Red Group 51C.
*Upon opening, petals.*—Outermost petals: Upper Surface: Yellow Group 7B at base, Yellow Group 9D at tip. Reverse Side: Yellow Group 9C. Innermost petals: Upper Surface: Yellow Group 9C. Reverse Side: Yellow Group 8C.
*Basal petal spots.*—No distinctive coloration at petal base observed.
*After opening, petals.*—Outermost petals: Upper Surface: Yellow Group 8C. Reverse Side: Yellow Group 8D. Innermost petals: Upper Surface: Yellow Group 8B. Reverse Side: Yellow Group 8C.
General tonality: On open flower, Yellow Group 8B. No change in the general tonality at the end of the 3rd day. Afterwards, general tonality is Yellow Group 8D.
Petals
*Petal reflex.*—Somewhat reflexed.
*Petal edge.*—Entire, with some undulation.
*Shape.*—Obovate, with notched, rounded and cuspidate apices.
*Petaloids.*—20 to 25. Petaloids are 7 to 10 mm long and 5 to 8 mm wide. Petaloid texture is smooth.
*Thickness.*—Average.
*Arrangement.*—Not formal.
Reproductive organs:
*Pollen.*—Color: Greyed-Orange Group 167C. Quantity: Scant.
*Pistils.*—Quantity: 25 to 30. Size: 8 to 10 mm.
*Anthers.*—Size: 3 to 4 mm long. Color: Greyed-Orange Group 167D. Quantity: 15 to 20.
*Filaments.*—Color: Yellow Group 7A.
*Stigmas.*—Inferior in location to anthers. Color: Yellow Group 12C with intonations of Red Group 51C.
*Styles.*—Color: Green-White Group 157C.
*Note on coloration of the flower center.*—The overall intonation of the reproductive floral organs is primarily due to the numerous petaloids. The petaloids have a base color of Yellow Group 12B, with intonations of Yellow Group 15B and Yellow Group 15C.
*Hips.*—None observed.

PLANT

Plant growth: Vigorous and bushy. After two growing seasons, when grown as a budded field grown plant on *Rosa multiflora* understock, the average height of the plant itself is 100–120 cm and the average width is 90 cm.
Stems:
*Color.*—Young wood: Green Group 145A. Older wood: Green Group 144B.
*Thorns.*—Incidence: 10 to 13 per 10 cm of stem. Size: 8 to 12 mm. Color: Immature thorns are Yellow-Green Group 151C. On older wood, thorns are Greyed-Orange Group 166A and 166D. Shape: Deeply concave.
*Surface.*—Young wood: Smooth. Older wood: Smooth.
Plant foliage: Normal number of leaflets on normal leaves in middle of the stem: 5 leaflets.

*Leaf size*.—Large 120 mm (l)×90 mm (w).

*Quantity*.—Abundant.

*Color*.—Upper Leaf Surface: Green Group 137A. Lower Leaf Surface: Green Group 138A. Juvenile foliage: Green Group 137C. Anthocyanin intonation: No.

Plant leaves and leaflets:

*Stipules*.—Size: 15 mm–20 mm. Color: Yellow-Green Group 144C. Presence of stipitate glands: Very limited on upper and lower surfaces. Stipitate glands are located primarily on the margins.

*Petiole*.—Length: 25 mm. Color: Yellow-Green Group 144C. Underneath: Prickles present. Margins: No stipitate hairs present.

*Rachis*.—Color: Yellow-Green Group 144D. Underneath: Prickles present. Margins: Stipitate hairs on upper surface.

*Leaflet*.—Edge: Serrated. Shape: Elliptic. The leaflet's apex is acuminate. The leaflet's base is rounded. Arrangement: The leaflets are arranged in an odd-pinnate formation. Venation: The leaflets are veined in a reticulate pattern. Texture: Upper side of leaflet is moderately glossy. Lower side of leaflet is matte.

Disease resistance: Above average resistance to mildew, black spot, and Botrytis under normal growing conditions in Jackson County, Oreg.

Winter hardiness: 'POULege' has been found to be resistant to damage from cold in USDA Zone 8 and USDA Zone 7.

We claim:

1. A new and distinct variety of rose plant of the floribunda class, substantially as herein illustrated and described as a distinct and novel rose variety due to its abundant, yellow flowers, vigorous growth, disease resistance, and extended period of bloom.

* * * * *

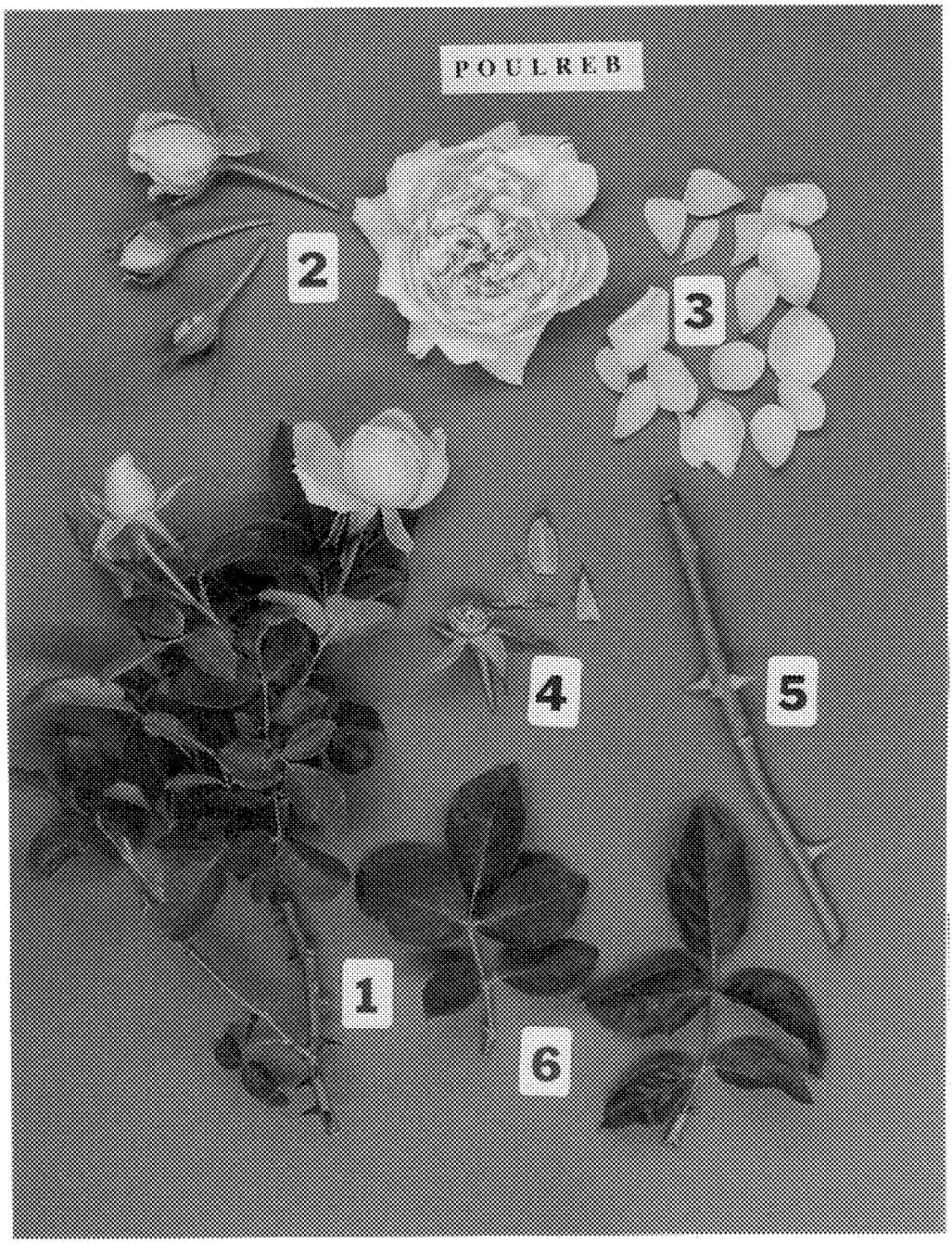
POULREB
2
3
4
5
1
6